United States Patent [19]

Stahl et al.

[11] 4,383,032

[45] May 10, 1983

[54] REAGENT FOR THE DETERMINATION OF β-LACTAMASE

[75] Inventors: Peter Stahl, Bernried; Wolfgang Vömel, Mannheim; Hans Seidel, Tutzing, all of Fed. Rep. of Germany

[73] Assignee: Boehringer Mannheim GmbH, Mannheim-Waldhof, Fed. Rep. of Germany

[21] Appl. No.: 265,267

[22] Filed: May 20, 1981

[30] Foreign Application Priority Data

May 21, 1980 [DE] Fed. Rep. of Germany ....... 3019451

[51] Int. Cl.³ .......................... C12Q 1/04; C12Q 1/06; C12Q 1/30; C12Q 1/38
[52] U.S. Cl. ........................................ 435/23; 435/27; 435/34; 435/39; 435/810; 435/25; 435/805
[58] Field of Search ................. 435/4, 23, 27, 29, 810, 435/34, 39, 25, 805, 299, 300, 301

[56] References Cited

U.S. PATENT DOCUMENTS 4,225,669 9/1980 Melnick et al. ...................... 435/29
4,234,683 11/1980 McMillan .............................. 435/29
4,311,794 1/1982 Melnick et al. ........................ 435/27

OTHER PUBLICATIONS

Madler et al., Applied and Environmental Microbiology, 32(4), 575–578 (1976).

*Primary Examiner*—Esther M. Kepplinger
*Attorney, Agent, or Firm*—Felfe & Lynch

[57] ABSTRACT

The present invention provides a process for the determination of β-lactamases by the use of 7-cyanoacetylaminocephalosporanic acid and measurement of the colored material thereby formed, wherein ammonium ions are added to the material to be tested, together with phosphate ions and/or an agent splitting off oxygen.

The present invention also provides a reagent for the determination of β-lactamases based upon 7-cyanoacetylaminocephalosporanic acid, which reagent additionally contains ammonium ions, together with phosphate ions and/or an agent splitting off oxygen.

20 Claims, No Drawings

REAGENT FOR THE DETERMINATION OF β-LACTAMASE

This invention relates to a method and a reagent for the determination of beta-lactamases. More specifically the invention relates to such a method and reagent using 7-cyanoacetylaminocephalosporanic acid.

Penicillins and cephalosporins, which are widely used antibiotics, are chemically characterised by the presence of a β-lactam ring. This β-lactam ring is split by a group of enzymes, which are referred to as β-lactamases, this splitting resulting in inactivation. Therefore, an important resistance mechanism of microbial gram-positive and gram-negative pathogens depends upon the formation of β-lactamases.

Hitherto, it was assumed that the β-lactamase activity of pathogens may also be dedected in the determination of resistance or the determination of the minimum inhibiting concentration (MIC). However, it has now been found that such a correlation does not exist. A pathogen recognised as being sensitive to a β-lactam antibiotic in the agar test can, nevertheless, be resistant in patients as a result of a β-lactamase activity formed in the course of a subsequent growth phase.

Therefore, there is a need for a practical routine test for β-lactamase activity as a supplement to the resistance determination with β-lactam antibiotics. Such a test should be able to detect, as specifically as possible, extracellular and periplasmatic β-lactamases and be capable of being carried out by means of a stable and sensitive indicator reaction.

β-Lactamase test is commercially available in which penicilloic acid is formed from benzylpenicillin, this acid being determined with an appropriate pH indicator. This method suffers from the disadvantage that it cannot be applied to extracellular β-lactamases, the pH indicator is non-specific, it is virtually impossible to use it to determine cephalosporin resistance and the sensitivity of the test is not sufficient for many β-lactamase producers.

A process is also known for the determination of β-lactamase by the addition of 7-cyanoacetylaminocephalosporanic acid (as sodium salt), a commercially available antibiotic known under the name of "cephacetril" (see Microbios Letters, 3, 35–39/1976). A red-coloured material is hereby formed in the presence of air, the amount of which material can be determined. However, this process cannot be used for a routine test since an incubation time of 24 hours at 37° C. is necessary for the color development.

We have now found that it is possible so to accelerate this color formation by means of certain additives that the test can be carried out in a few minutes, and the sensitivity of this test may be adjusted to meet different requirements.

Thus, according to the present invention, there is provided a process for the determination of β-lactamases by the use of 7-cyanoacetylaminocephalosporanic acid and measurement of the coloured material thereby formed, wherein ammonium ions are added to the material to be tested, together with phosphate ions and/or an agent splitting off oxygen.

According to a preferred embodiment of the present invention, use is made of all three additives, i.e. ammonium ions, phosphate ions and an agent splitting off oxygen.

Neither ammonium ions nor phosphate ions alone exert an accelerating action on the color formation. It was, therefore, surprising that the combined use of these two ions has a synergistic effectiveness which results in a very considerable acceleration of the color-formation reaction. It was not to have been expected that an agent splitting off oxygen would substantially increase the speed of the color-forming reaction since atmospheric oxygen is, of course, always present in excess.

The agent splitting off oxygen is preferably catalase, together with hydrogen peroxide. The hydrogen peroxide can be added as such, i.e. in liquid form, or in the form of an adduct, which is usually in solid form, or in the form of a system which provides hydrogen peroxide. The agent or system providing hydrogen peroxide may, within the scope of the present invention, be an oxidase, together with its reducing substrate. Examples thereof include glucose oxidase and glucose, cholesterol oxidase and cholesterol, xanthine oxidase and xanthine, and diaminooxidase and an amine, such as hexamethylenediamine, histamine or the like. Examples of hydrogen peroxide adducts which may be used include urea peroxyhydrate, phosphate peroxyhydrates, borate peroxyhydrates and carbonate peroxyhydrates, preferably in the form of ammonium salts. Because of the content of ammonium ions, phosphate ions and hydrogen peroxide, ammonium peroxyphosphate is particularly preferred.

Ammonium ions are added in the form of an appropriate salt, for example as phosphate, chloride or sulphate. The phosphate ions are preferably used in the form of alkali metal salts, these preferably simultaneously serving to adjust the pH value. For the reaction itself, adjustment is made to a pH value at which the β-lactamases to be determined are active. In general, well suited pH values are from 5.5 to 8.5, the range of from 6.5 to 7 being preferred.

The process according to the present invention can be carried out at ambient temperature or at an elevated temperature. Since the β-lactamases are relatively temperature stable, it is preferable to carry out the process at an elevated temperature of from 30° to 65° C.

The process according to the present invention can be carried out in the usual manner as a cuvette test, not only by the end point method but also kinetically. At a reaction temperature of 60° C., and with the addition of ammonium ions, phosphate ions and hydrogen peroxide, the end point of the reaction is reached after 5 minutes, whereas at 37° C., the end point is reached after 10 to 15 minutes. Therefore, at this temperature, a kinetic process is preferred. However, the process according to the present invention may also be used for the microtiter test, strip test or plate test. In the case of the microtiter, strip or plate test, the sensitivity is increased, especially in the case of gram-negative microorganisms, by the addition of a complex former, for example ethylenediamine-tetraacetic acid (EDTA) and/or of a detergent and/or of an appropriate antibiotic. It is assumed that the permeability of the gram-negative cells is increased by the detergent and/or the complex former and/or antibiotic.

According to an especially preferred embodiment of the process according to the present invention, when carrying out the test on a culture plate and especially on an inoculated or pre-incubated culture plate, the reagents necessary for the reaction are applied to one point on the surface of the culture and a barrier which is impermeable to the coloured material formed is placed round this point. This barrier is preferably an annular member made of synthetic resin, glass or metal, a ring of appropriate diameter being applied, for example by pressing in, round the point of application of the reagent to the culture. In this manner, a diffusing out of the colored material formed into the plate is prevented and the exactitude of the measurement of the coloured material is increased. The measurement itself can be carried out visually, for example by comparison with a color scale, or by determination of the absorption between about 400 and 600 nm.

The acceleration of the colored material formation which can be achieved according to the present invention occurs within a very wide range of concentrations of the phosphate ions, ammonium ions and hydrogen peroxide. Preferably, the concentration of the phosphate ions should be 0.001 to 1 mol/liter of the ammonium ions 0.01 to 3 mol/liter and of the hydrogen peroxide 0.01 to 0.5 mol/liter, the best results being obtained with a phosphate ion concentration of 0.01 to 0.1 mol/liter, an ammonium ion concentration of 0.2 to 1 mol/liter and a hydrogen peroxide concentration of 0.05 to 0.2 mol/liter.

The present invention also provides a reagent for the determination of β-lactamases based upon 7-cyanoacetylaminocephalosporanic acid, which reagent additionally contains ammonium ions, together with phosphate ions and/or an agent splitting off oxygen.

According to a preferred embodiment of the reagent according to the present invention, it contains 0.1 to 100 mg./ml. 7-cyanoacetylaminocephalosporanic acid,
0.01 to 0.5 mol hydrogen peroxide per liter,
0.001 to 0.5 mol phosphate ions per liter,
0.01 to 3 mol ammonium ions per liter,
2.5 to 100 mMol/ml. EDTA or of a detergent and
5 to 1000 U catalase per test, and has a pH value of from 5.5 to 8.5.

The reagent can be in the form of a dry mixture of the solid substances which, before use, is made up with water to the stated concentration or it can also be present in dissolved form.

According to a special embodiment of the reagent according to the present invention, it is impregnated into an absorbent, inert carrier. The carrier can be, for example, a paper strip or platelet, an absorbent synthetic resin film, granular absorbent material or the like, this embodiment being especially useful for a plate test. It then suffices to place an appropriately impregnated platelet on the point of the culture to be investigated, to moisten it with water and to determine the color formed. The above-mentioned embodiment using an impermeable barrier layer is hereby preferably employed. Thus, a ring of synthetic resin, metal or glass with a diameter which corresponds to or is greater than that of the platelet is applied to and pressed into the culture plate so that the color formed remains concentrated within this ring.

This system can preferably serve as a supplement to the determination of resistance since a pathogen recognised as being sensitive towards a β-lactam antibiotic in the agar diffusion test can, nevertheless, as a result of its β-lactamase activity formed in a later growth phase, prove to be resistant in patients. For this purpose, on to already grown micro-organism smears, a test platelet and a barrier layer (for example a synthetic resin cylinder) are applied and the test plate is further incubated. The red coloration of the test platelet shows the formation of extracellular or periplasmatic β-lactamase production during the growth of the micro-organism.

The process and reagent according to the present invention can be used for the determination of all β-lactamases (penicillinase/cephalosporinase). As examples, there may be mentioned β-lactamase I and II from *Bacillus cereus*, TEM-β-lactamase from *Escherichia coli* and β-lactamases from *Enterobacter cloacae*, from *Staphylococcus aureus* and from *Aerobacter aerogenes*.

With the process according to the present invention, β-lactamase concentrations of down to 0.05 U/ml. can be detected. Because of its high degree of sensitivity, the process may also be used for a general detection of micro-organisms and especially of gram-negative bacteria, for example in urine.

The following Examples are given for the purpose of illustrating the present invention:

EXAMPLE 1

26U Catalase (10 μl. of a commercially available preparation diluted 1:100), 20 μl. of 3.3% hydrogen peroxide solution, 2 ml. of a 0.1 mol/liter phosphate buffer (pH 6.5) and 200 μl. of a saturated ammonium sulphate solution, as well as 100 μl. 7-cyanoacetylaminocephalosporanic acid (c=100) are pipetted into a cuvette and heated to 60° C. 170 μl. of a lactamase-containing test solution are then added thereto. After 10 minutes, the extinction is determined at 546 nm.

Example 2

Microtiter Test 10 l. Catalase solution (26 U), 20 μl. of 3.3% hydrogen peroxide solution, 100 μl. of 0.1 mol/l. phosphate buffer (pH 7), 20 μl. saturated ammonium sulphate solution and 10 μl. 7-cyanoacetylaminocephalosporanic acid (c=100) are mixed with 50 μl. of test solution and heated to 60° C. for 5 minutes. The red coloration formed is semi-quantitatively determined by means of a comparative scale.

Example 3

10 l. Catalase solution (26 U), 20 μl. of 3.3% hydrogen peroxide solution, 10 μl. of 1 mol/l. phosphate buffer (pH 7), 20 μl. saturated ammonium sulphate solution and 10 μl. 7-cyanoacetylaminocephalosporanic acid (c=100) are mixed with 200 μl. liquid culture and heated for 5 minutes to 60° C. The red colour formed is semi-quantitatively determined by means of a comparative scale.

Example 4

Filter paper, especially filter leaflets with a diameter of 6 to 9 mm., is impregnated with a solution which contains 100 U catalase/ml., 1 mol urea peroxyhydrate/liter, 0.5 mol ammonium sulphate/liter in 0.1 molar phosphate buffer (pH 6.5), 1 g./liter 7-cyanoacetylaminocephalosporanic acid and 1 g./liter of a non-ionic detergent or 25 mMol EDTA. The impregnated filter paper is dried and cut up into 1 cm. wide strips.

The so obtained test strips/platelets are laid on to the surface of an inoculated agar culture plate. A synthetic resin ring of 1.5 cm. or of 0.7 to 1.0 cm. diameter and 10 mm. height is placed over the leaflet on the agar plate and pressed into the agar. After development for 5 minutes at 60° C., the now red-colored leaflet is removed and its colour strength is determined with the help of a comparative scale.

It will be understood that the specification and examples are illustrative but not limitative of the present invention and that other embodiments within the spirit and scope of the invention will suggest themselves to those skilled in the art.

What is claimed is:

1. Method for the determination of beta-lactamases comprising contacting the sample to be determined with 7-cyanoacetylaminocephalosporanic acid in an amount to form a quantitative color reaction and, in amounts effective to accelerate the color reaction, a synergistic mixture of ammonium ions and at least one member of the group consisting of phosphate ions and oxygen-splitting agents; and measuring the colored material formed as a measure of the beta-lactamases present.

2. Method as claimed in claim 1, wherein ammonium ions and phosphate ions are added.

3. Method as claimed in claim 1, wherein ammonium ions and an oxygen-splitting agent are added.

4. Method as claimed in claim 1, wherein ammonium ions, phosphate ions and an oxygen-splitting agent is added.

5. Method as claimed in claim 3, wherein said oxygen-splitting agent is catalase, together with hydrogen peroxide or a compound releasing hydrogen peroxide.

6. Method as claimed in claim 5, wherein the compound releasing hydrogen peroxide is an oxidase and its reducing substrate.

7. Method as claimed in claim 5, wherein the hydrogen peroxide releasing compound is a hydrogen peroxide adduct.

8. Method as claimed in claim 7, wherein the hydrogen peroxide adduct is urea peroxyhydrate or a phosphate peroxyhydrate.

9. Process as claimed in claim 1, wherein the color forming reaction is carried out at elevated temperature.

10. Process for the determination of beta-lactamases which comprises contacting the sample to be determined with a combination of reagents consisting of 7-cyanoacetylaminocephalosporanic acid, ammonium ions, and at least one member of the group consisting of phosphate ions and oxygen-splitting agents, with a portion of the reagent combination being on the surface of a culture plate and with a barrier layer impermeable to the colored reaction product formed being provided in the culture surrounding said portion.

11. Process as claimed in claim 10, wherein an annular barrier member of synthetic resin, metal or glass is introduced into the culture around the portion of application of the reagents.

12. Method as claimed in claim 4, wherein there are used phosphate ions with a molarity of 0.001 to 1 mol/liter, ammonium ions with a molarity of 0.01 to 3 mol/liter and/or hydrogen peroxide with a molarity of 0.01 to 0.5 mol/liter.

13. Reagent for the colorimetric determination of beta-lactamases by reaction with 7-cyanoacetylaminocephalosporanic acid, comprising:
7-cyanoacetylaminocephalosporanic acid, and in amounts effective to accelerate the color reaction, a synergistic mixture of ammonium ions, and
at least one member of the group consisting of phosphate ions, and oxygen splitting agents.

14. Reagent as claimed in claim 13, containing ammonium ions together with phosphate ions.

15. Reagent as claimed in claim 13, containing ammonium ions together with an oxygen-splitting agent.

16. Reagent as claimed in claim 13, containing ammonium ions, phosphate ions and an oxygen-splitting agent.

17. Reagent as claimed in claim 13, containing
0.1 to 100 mg./ml. 7-cyanoacetylaminocephalosporanic acid,
0.01 to 0.5 mol hydrogen peroxide per liter,
0.001 to 0.5 mol phosphate ions per liter,
0.01 to 3 mol ammonium ions per liter,
2.5 to 100 mMol/liter EDTA or of a detergent and
5 to 1000 U catalase per test volume,
and has a pH value of 5.5 to 8.5.

18. Reagent as claimed in claim 17, impregnated into a solid, absorbent carrier material.

19. Reagent as claimed in claim 13, containing a substance which makes the outer bacterial membranes more permeable.

20. Reagent as claimed in claim 19, wherein the substance is a detergent, a chelate former (EDTA) and/or an antibiotic.

* * * * *